United States Patent
Song

(10) Patent No.: US 11,020,607 B2
(45) Date of Patent: Jun. 1, 2021

(54) DEVICE FOR ACTIVATING MASK PACK, PHOTON THERAPY MASK PACK DEVICE, AND FIBER BASED LIGHT EMITTING LIGHTING DEVICE

(71) Applicant: TEDDY KOREA, Seoul (KR)

(72) Inventor: In Sil Song, Seoul (KR)

(73) Assignee: TEDDY KOREA, Seoul (KR)

( * ) Notice: Subject to any disclaimer, the term of this patent is extended or adjusted under 35 U.S.C. 154(b) by 163 days.

(21) Appl. No.: 15/668,585

(22) Filed: Aug. 3, 2017

(65) Prior Publication Data

US 2019/0038912 A1   Feb. 7, 2019

(51) Int. Cl.
*A61N 5/00*   (2006.01)
*A61N 5/06*   (2006.01)
*A45D 44/00*   (2006.01)

(52) U.S. Cl.
CPC ......... *A61N 5/0616* (2013.01); *A45D 44/002* (2013.01); *A61N 2005/066* (2013.01); *A61N 2005/0647* (2013.01); *A61N 2005/0652* (2013.01); *A61N 2005/0659* (2013.01)

(58) Field of Classification Search
CPC .......... A61N 5/0616; A61N 2005/0647; A61N 2005/0652; A61N 2005/0659; A61N 2005/066; A61N 2005/0645; A45D 44/002
See application file for complete search history.

(56) References Cited

U.S. PATENT DOCUMENTS

| 5,891,516 A | * | 4/1999 | Gstrein | B28B 1/527 |
| | | | | 427/189 |
| 9,597,527 B2 | * | 3/2017 | Buchholz | A61N 5/0616 |
| 2006/0217787 A1 | * | 9/2006 | Olson | A61N 5/0616 |
| | | | | 607/88 |

(Continued)

FOREIGN PATENT DOCUMENTS

| KR | 100922684 B1 | * | 10/2009 | C09J 133/14 |
| KR | 20160095878 A | * | 8/2016 | |

(Continued)

OTHER PUBLICATIONS

Comparing flip-chip and wire bond interconnection technologies" to Elenius et al. (hereinafter"Elenius (Year: 2010).*

*Primary Examiner* — Rex R Holmes
*Assistant Examiner* — Sana Sahand
(74) *Attorney, Agent, or Firm* — Ichthus International Law PLLC

(57) ABSTRACT

Disclosed herein is a device for activating a mask pack, a photon therapy mask pack device, and a fiber based light emitting lighting device. The device for activating a mask pack includes: a first fiber fabric layer having a shape corresponding to that of a face of a wearer and having ductility for being closely adhered to the face of the wearer; a metal pattern layer attached to one surface of the first fiber fabric layer; an insulating resin adhesive layer attaching the first fiber fabric layer and the metal pattern layer to each other; a light emitting diode element attached onto the metal pattern layer and irradiating photon therapy light; an adhesive film layer covering the metal pattern layer and the light emitting diode element and in contact with the mask pack; and a power supplying module supplying power to the light emitting diode element to allow components of the mask pack to be better permeated into a skin of the wearer.

16 Claims, 5 Drawing Sheets

(56) References Cited

U.S. PATENT DOCUMENTS

| | | | |
|---|---|---|---|
| 2007/0233208 A1* | 10/2007 | Kurtz | A61N 5/0613 607/88 |
| 2013/0184693 A1* | 7/2013 | Neev | A61B 18/18 606/9 |
| 2019/0009102 A1* | 1/2019 | Mori | A61N 5/0616 |
| 2019/0290929 A1* | 9/2019 | Jiao | H01L 51/56 |

FOREIGN PATENT DOCUMENTS

| | | | | |
|---|---|---|---|---|
| KR | 20170108533 A | * | 9/2017 | |
| KR | 101823263 B1 | * | 1/2018 | |
| KR | 101855946 B1 | * | 5/2018 | |
| WO | WO-2018182149 A1 | * | 10/2018 | A45D 44/22 |

* cited by examiner

DEVICE FOR ACTIVATING MASK PACK, PHOTON THERAPY MASK PACK DEVICE, AND FIBER BASED LIGHT EMITTING LIGHTING DEVICE

BACKGROUND

Field

The present invention relates to a device for activating a mask pack and a photon therapy mask pack device.

Description of the Related Art

Generally, an aging phenomenon of a skin of a human body starts while a person passes his/her last 20s, such that he/she starts to have wrinkles and a phenomenon in which elasticity of the skin is lost occurs. As a means for suppressing such an aging phenomenon, functional applying agents such as various cosmetics, massage cream, and the like, have been conventionally used. However, recently, the use of the functional applying agents has gradually decreased due to a side effect such as various skin diseases.

In accordance with such a trend, skin care specialty stores called various skin cares, make-up, or the like, have been recently prevalent. As a skin care manner in the skin care specialty stores (in an example of a facial portion), a manner of appropriately applying nourishing cream, functional oil, or the like, for removing wrinkle and caring a skin to the facial portion and then allowing a wearer to wear a mask for a predetermined time to provide a massage effect obtained from the mask to the wearer has been mainly adopted.

In this case, the nourishing cream or the functional oil should be permeated well into the skin. Particularly, in the case of an old person of which a skin aging phenomenon is large, the oil, or the like, is not permeated well into the skin, such that a massage effect is small or the mask pack should be maintained for a long period of time, which is problematic.

SUMMARY

An object of the present invention is to provide a device for activating a mask pack and a photon therapy mask pack device capable of maximizing a mask pack effect by allowing oil or nourishing components of a mask pack attached to a face to be permeated well into a derma layer as well as an epidermis layer of the face.

According to an exemplary embodiment of the present invention, a device for activating a mask pack includes: a first fiber fabric layer having a shape corresponding to that of a face of a wearer and having ductility for being closely adhered to the face of the wearer; a metal pattern layer attached to one surface of the first fiber fabric layer; an insulating resin adhesive layer attaching the first fiber fabric layer and the metal pattern layer to each other; a light emitting diode element attached onto the metal pattern layer and irradiating photon therapy light; an adhesive film layer covering the metal pattern layer and the light emitting diode element and in contact with the mask pack; and a power supplying module supplying power to the light emitting diode element to allow components of the mask pack to be better permeated into a skin of the wearer.

The light emitting diode element may be a flip-on-chip light emitting diode.

A surface of the adhesive film layer may be embossing-processed in order to increase an adhesion property with the mask pack.

The adhesive film layer may be formed of a transparent silicone resin.

A plurality of wrinkle parts configured in a concentric circle shape may be formed on the surface of the adhesive film layer.

The device for activating a mask pack may further include a second fiber fabric layer attached to the other surface of the first fiber fabric layer.

The first fiber fabric layer may have an electrical insulation property, and the second fiber fabric layer may have thermal conductivity more excellent than that of the first fiber fabric layer.

The second fiber fabric layer may include: a plurality of external fiber bundles famed to be orthogonal to each other; and internal fiber bundles formed in a space formed by the external fiber bundles.

The light emitting diode element may include: a first sub light emitting diode having a wavelength band of 600 to 680 nm; and a second sub light emitting diode having a wavelength band of 800 to 980 nm, and the first sub light emitting diode and the second sub light emitting diode may be alternately installed.

The device for activating a mask pack may further include a coupling screw fitted into a coupling hole formed in the adhesive film layer in order to fix the mask pack.

According to another exemplary embodiment of the present invention, a photon therapy mask pack device includes: a mask pack; a first fiber fabric layer having a shape corresponding to that of a face of a wearer and having ductility for being closely adhered to the face of the wearer; a metal pattern layer attached to one surface of the first fiber fabric layer; an insulating resin adhesive layer attaching the first fiber fabric layer and the metal pattern layer to each other; a light emitting diode element attached onto the metal pattern layer and irradiating photon therapy light to the mask pack; an adhesive film layer covering the metal pattern layer and the light emitting diode element, in contact with the mask pack, and having a surface that is embossing-processed; and a power supplying module supplying power to the light emitting diode element.

According to still another exemplary embodiment of the present invention, a fiber based light emitting lighting device includes: a heat dissipation fiber fabric layer having a plurality of fiber bundles formed to be orthogonal to each other; a metal pattern layer attached onto the heat dissipation fiber fabric layer; an insulating resin adhesive layer attaching the heat dissipation fiber fabric layer and the metal pattern layer to each other; and a light emitting diode element attached onto the metal pattern layer, wherein the heat dissipation fiber fabric layer includes: an internal fiber bundle having an oval shape; and an external fiber bundle surrounding an outer surface of the internal fiber bundle, and thermal conductivity of the internal fiber bundle is higher than that of the external fiber bundle so that heat is well radiated in the heat dissipation fiber fabric layer.

The fiber based light emitting lighting device may further include a CNT layer formed between the insulating resin adhesive layer and the metal pattern layer.

DETAILED DESCRIPTION

Hereinafter, a device for activating a mask pack and a photon therapy mask pack device according to an exemplary embodiment of the present invention will be described in more detail with reference to the drawings.

Figure 1:
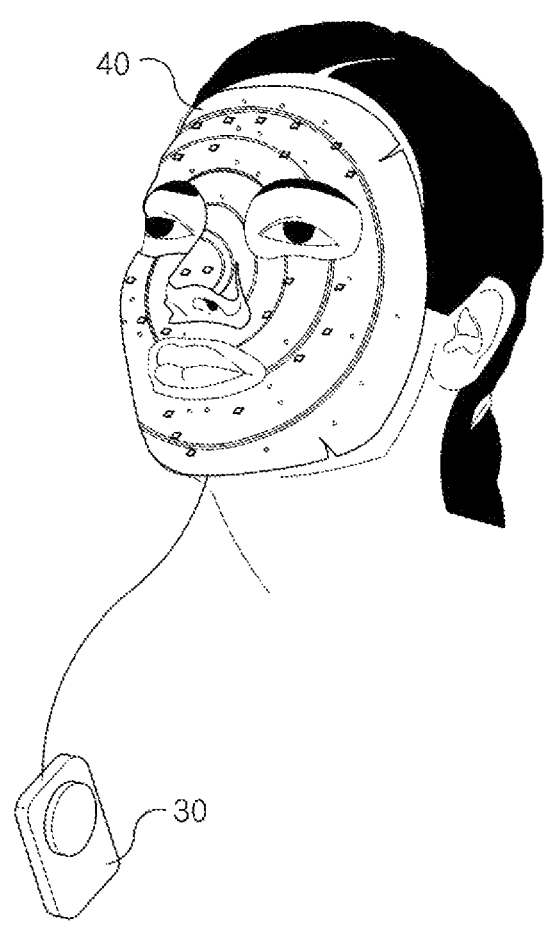
FIG. 1 is a view illustrating an example in which a user wears a device for activating a mask pack according to an exemplary embodiment of the present invention.

FIG. 1 is a view illustrating an example in which a user wears a device for activating a mask pack according to an exemplary embodiment of the present invention. As illustrated in FIG. 1, a user attaches and uses the device for activating a mask pack according to an exemplary embodiment of the present invention to a mask pack M in a state in which he/she attaches the mask pack M to his/her face. When the device for activating a mask pack is used as described above, a derma layer and an epidermis layer may be activated by photon therapy light generated in the device for activating a mask pack, and heat by a light emitting diode (LED) has a thermotherapy effect. The light massage effect and the thermotherapy effect as described above are added to each other, such that nourishing components of the mask pack M are better permeated into a skin of the face, thereby making it possible to maximize an effect of the mask pack M. In addition, the device for activating a mask pack according to an exemplary embodiment of the present invention has a structure in which light emitting diode elements 14 emit light through a power supplying module 30. In the case in which a small battery such as a mercury battery is used as the power supplying module 30, the user attaches and uses the power supplying module 30 to one side of the device for activating a mask pack, thereby making it possible to simply use the device for activating a mask pack anytime and anywhere without needing to connect the device for activating a mask pack to a separate commercial power supply.

In addition, the device for activating a mask pack according to an exemplary embodiment of the present invention may become a trade target as a set with the mask pack. This case may be defined as a photon therapy mask pack device.

Hereinafter, the device for activating a mask pack will be described in more detail with reference to FIGS. 2 to 5.

Figure 2:
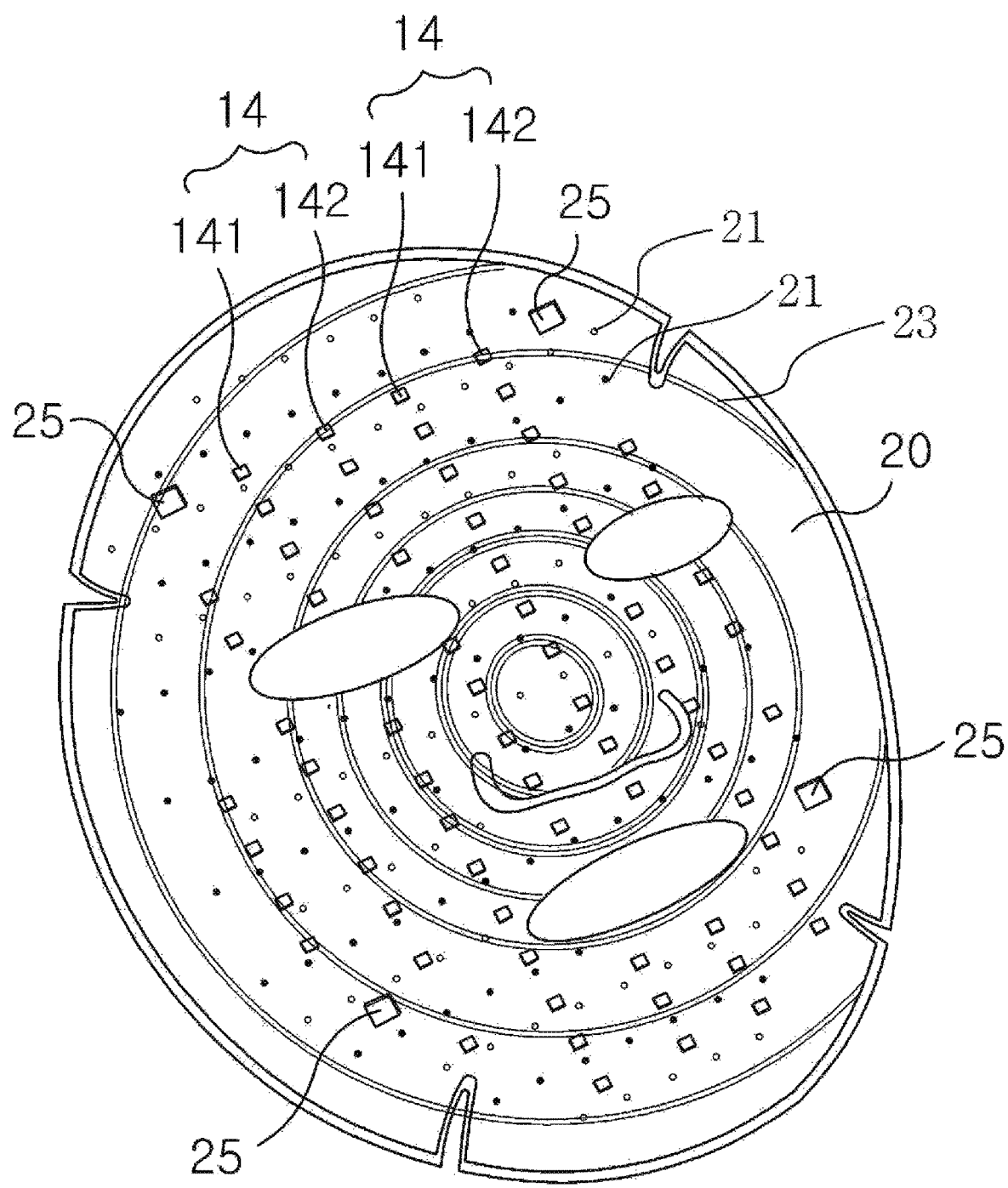
FIG. 2 is a view for describing an adhesive film layer of the device for activating a mask pack according to an exemplary embodiment of the present invention.
Figure 3:
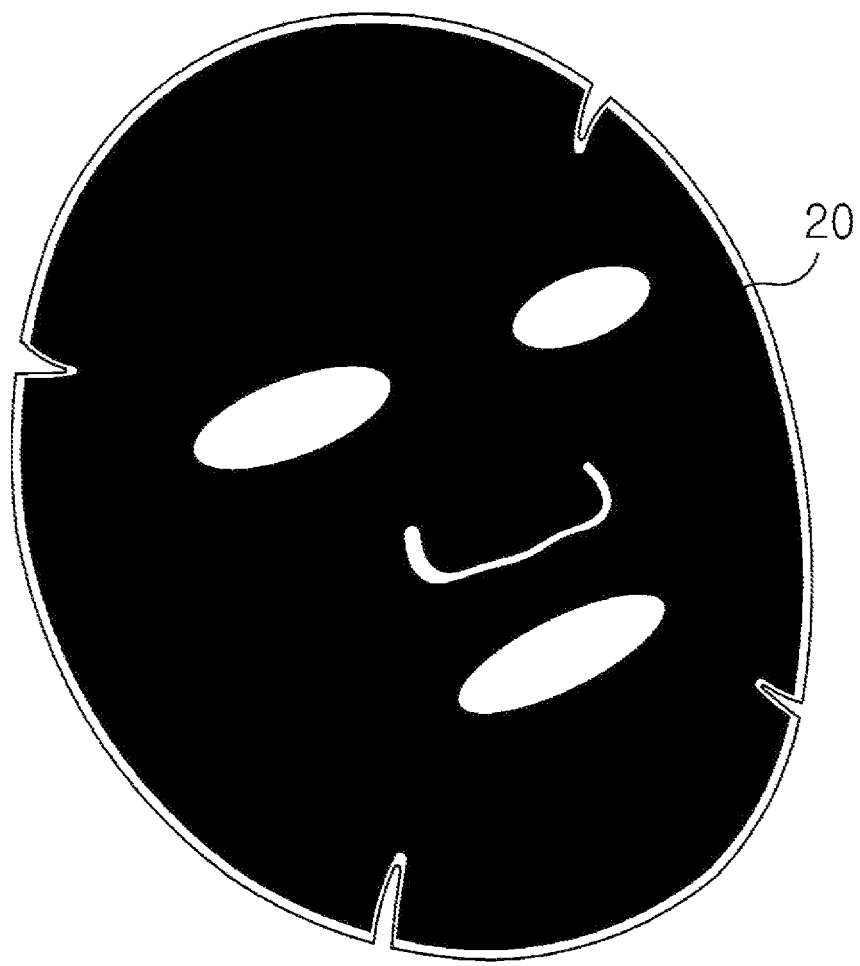
FIG. 3 is a rear view of the device for activating a mask pack according to an exemplary embodiment of the present invention.
Figure 4:
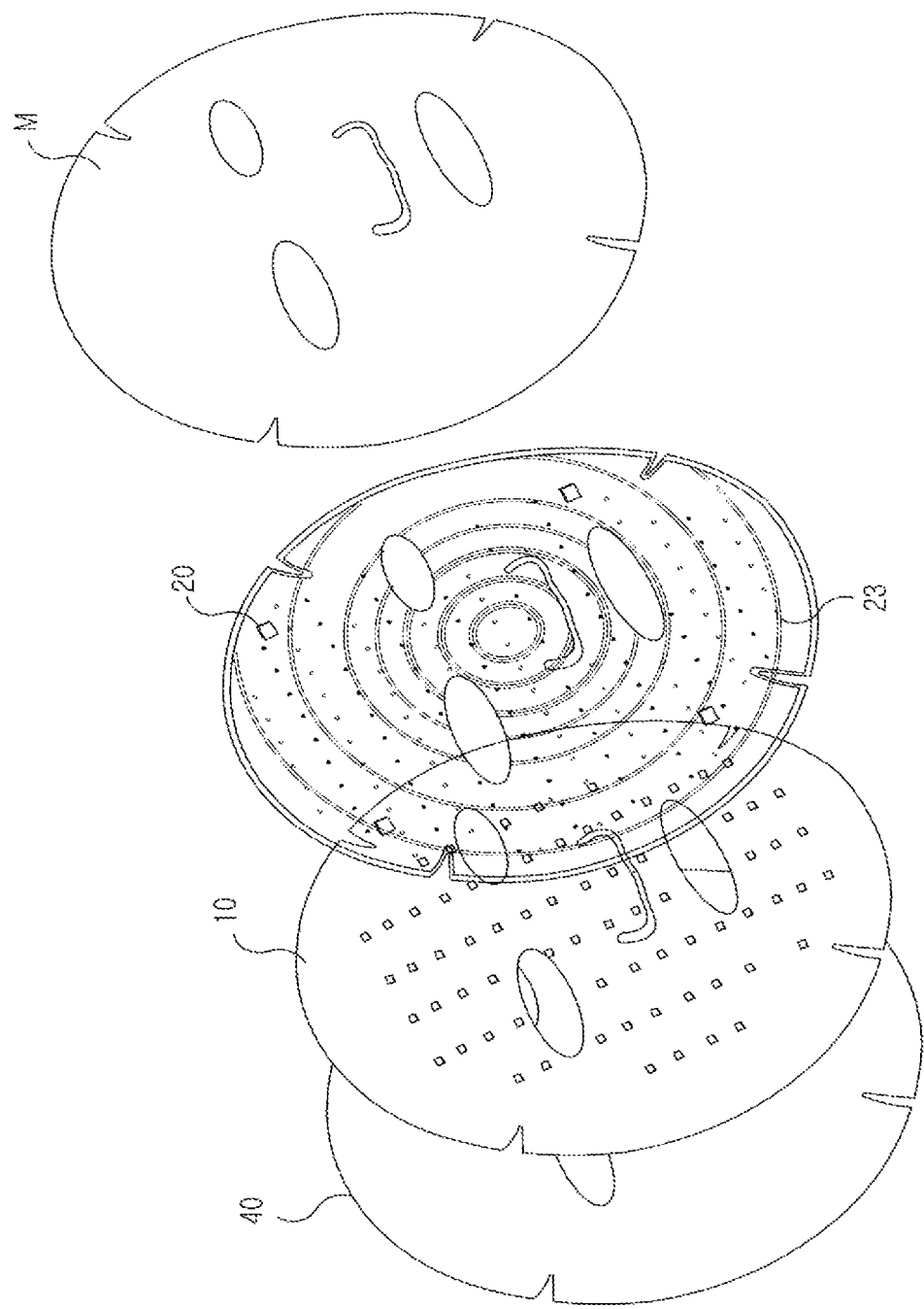
FIG. 4 is an exploded perspective view of the device for activating a mask pack according to an exemplary embodiment of the present invention.

FIG. 2 is a view for describing an adhesive film layer 20 of the device for activating a mask pack according to an exemplary embodiment of the present invention, and FIG. 3 is a rear view of the device for activating a mask pack according to an exemplary embodiment of the present invention. As illustrated in FIG. 2, the adhesive film layer 20 is attached to a front surface of the device for activating a mask pack, and generally has the same shape as that of a general mask pack M, and it may be confirmed that a plurality of light emitting diode elements 14 attached to a lower surface of the adhesive film layer 20 are disposed in a matrix form and the adhesive film layer 20 is embossing-processed in order to increase a contact property with the mask pack. In addition, as illustrated in FIG. 3, a second fiber fabric layer functioning as a heat dissipation sheet 40 (as shown in FIG. 4) is attached to a rear surface of the device for activating a mask pack. The second fiber fabric layer serves to outwardly dissipate heat of the light emitting diode elements 14.

Again referring to FIG. 2, the adhesive film layer 20 includes a plurality of wrinkle parts 23 formed in a concentric circle shape in order to uniformly irradiate photon therapy light. Therefore, the photon therapy light is better guided by the wrinkle parts 23, such that a refraction phenomenon occurs, and the photon therapy light of the light emitting diode elements 14, which are dot light sources, becomes a surface light source. Therefore, more excellent uniform light is irradiated to a face of a wearer. In addition, a surface of the adhesive film layer 20 is embossing-processed in order to increase an adhesion property to the mask pack. This embossing 21 not only increases the adhesion property, but also generates scattering or refraction of light, thereby making it possible to further improve a light effect of the photon therapy light. In addition, coupling grooves 25 may be formed in order to fix the device for activating a mask pack to the mask pack. That is, the device for activating a mask pack is simply coupled to the mask pack by a member such as screws, pins, or the like, such that separation between the mask pack M and the device for activating a mask pack that are being used may be prevented.

Meanwhile, the light emitting diode elements 14 may be configured to include first light emitting diodes and second light emitting diodes. In other words, the first light emitting diodes and the second light emitting diodes may be installed to intersect with each other. Here, the first light emitting diodes may have a wavelength band of 600 to 680 nm, which is a wavelength band of near infrared light, and the second light emitting diodes may irradiate light in a wavelength band of 800 to 980 nm, which is a wavelength band of far infrared light. Through the configuration as described above, the derma layer as well as the epidermis layer of the wearer are activated, such that the nourishing components of the mask pack M are better permeated into the skin of the wearer.

Hereinafter, a more detailed description will be provided through an exploded perspective view of the device for activating a mask pack.

FIG. 4 is an exploded perspective view of the device for activating a mask pack according to an exemplary embodiment of the present invention. As illustrated in FIG. 4, the device for activating a mask pack according to an exemplary embodiment of the present invention may be configured to include the adhesive film layer 20 in direct contact with the mask pack, a light emitting sheet 10 attached to the adhesive film layer 20, and the heat dissipation sheet 40 attached to a rear surface of the light emitting sheet 10.

The adhesive film layer 20 serves to cover the light emitting sheet 10, and diffuse photon therapy light generated from the light emitting sheet 10 (have translucency), and alleviate heat generated from the light emitting sheet 10. In order to diffuse the light, a light diffusion material is included in the adhesive film layer 20. Here, a silicon powder, or the like, may be used as the light diffusion material. The adhesive film layer 20 may be formed of a transparent silicone resin or be famed of a transparent urethane resin to have excellent ductility and low thermal conductivity.

The light emitting sheet 10 is a component having a shape corresponding to that of the face of the wearer and including the plurality of light emitting diode elements 14 installed thereon to irradiate the photon therapy light. A shape of the device for activating a mask pack including the light emitting sheet 10 needs to be freely changed like the mask pack M in order for the device for activating a mask pack to be closely adhered to the face of the wearer. To this end, in the present invention, a fiber fabric is used as a substrate. A configuration of the light emitting sheet 10 will be described in more detail with reference to FIG. 5.

The heat dissipation sheet 40 serves to outwardly heat generated from the light emitting sheet 10. The light emitting diode elements 14 of the light emitting sheet 10 are heat sources. In the case in which these heat sources have a direct or indirect influence on the wearer, a burn needs to be considered. The reason is that the wearer gets a burn when a thermotherapy function is excessive. In addition, the heat dissipation sheet 40 needs to have very excellent ductility together with the light emitting sheet 10 in order to have ductility so as to correspond to the face of the wearer. To this end, the heat dissipation sheet 40 is also formed of a fiber fabric. This will be described in more detail with reference to FIG. 5.

Hereinafter, structures of the light emitting sheet 10 and the heat dissipation sheet 40 of the device for activating a mask pack according to an exemplary embodiment of the present invention will be described with reference to FIG. 5.

Figure 5:
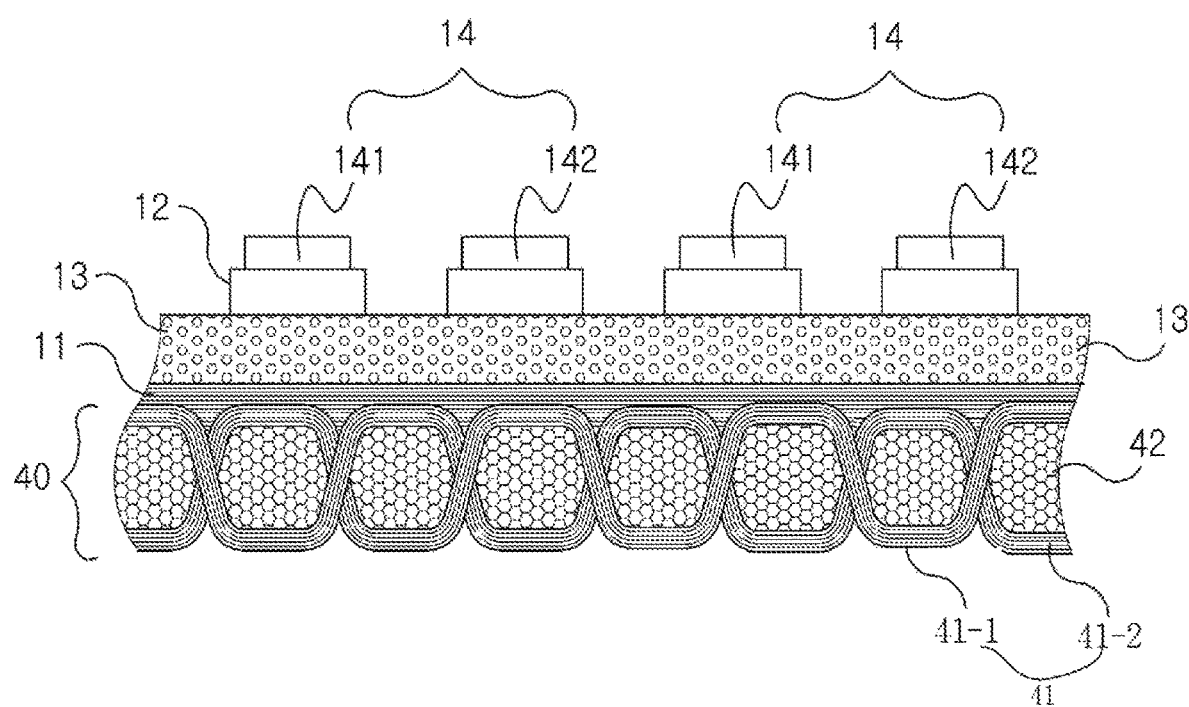
FIG. 5 is a cross-sectional view for describing a light emitting sheet and a heat dissipation sheet of the device for activating a mask pack according to an exemplary embodiment of the present invention.

FIG. 5 is a cross-sectional view for describing a light emitting sheet 10 and a heat dissipation sheet 40 of the device for activating a mask pack according to an exemplary embodiment of the present invention. In FIG. 5, a first fiber fabric layer 11, a metal pattern layer 12, an insulating resin adhesive layer 13, the light emitting diode elements 14, and a second fiber fabric layer are illustrated. Here, the first fiber fabric layer 11, the metal pattern layer 12, the insulating resin adhesive layer 13, and the light emitting diode elements 14 are included in the light emitting sheet 10, and the second fiber fabric layer corresponds to the heat dissipation sheet 40.

The first fiber fabric layer 11 serves as a substrate of the light emitting sheet 10. The device for activating a mask pack according to an exemplary embodiment of the present invention needs to have excellent ductility in order to be closely adhered to the face of the wearer. A substrate based on a fiber rather than a simple flexible substrate is used. The insulating resin adhesive layer 13 is formed on the first fiber fabric layer 11, and the metal pattern layer 12 is formed on the insulating resin adhesive layer 13. The first fiber fabric layer 11 may be formed of a bundle of a plurality of fibers that are orthogonal to each other. A fiber indicates a natural or artificial linear object that is long and thin and is bendable. The plurality of fibers may be woven by a weaving manner to become a fabric or be woven by a knitting manner to become a knit. The plurality of fibers may include carbon fibers (that are components constituting a bundle of carbon filaments). The carbon fiber is a carbon material where the mass content of carbon elements is 90% or more. The carbon fiber means a fiber obtained by thermally decomposing polyacrylonitrile, pitch (asphalt), which is a petroleum coal-based hydrocarbon residue, or an organic precursor material (material before being carbonized) made from rayon and having a fiber form at the inert atmosphere.

Specific heat of the carbon fiber is 0.7 to 0.9 kJ/Kg·K (an average value from room temperature to 70° C.), which is substantially the same as 0.5 to 1.0 kJ/Kg·K (from room temperature to 100° C.) of an alloy of iron, aluminum, and titanium and is about ½ of 1.5 to 2.0 kJ/Kg·K of plastic. The specific heat of the carbon fiber becomes large when a temperature becomes high, and an average value of the specific heat of the carbon fiber from room temperature to 1,500° C. is 1.7 kJ/Kg·K. Thermal conductivity of the carbon fiber is 390 to 750 W/m·K, which is 1.5 to 2 times larger than that of a metal.

As the carbon fiber, there are various products depending on performance, a form, a manufacturing method, and a raw material. As the carbon fiber, there are a small tow in which one bundle has 1,000 to 12,000 unit fibers and a large tow in which one bundle has 48,000 to 320,000 unit fibers.

The insulating resin adhesive layer 13 is a component for attaching the metal pattern layer 12 to the first fiber fabric layer 11. The insulating resin adhesive layer 13 may include a resin and ceramic powders for increasing thermal conductivity.

The resin, which is a thermosetting or thermoplastic resin, may include at least one of an acryl based resin, a silicone based resin, an urethane based resin, a polyimide based resin, an epoxy based resin, and a peek (PEEK) based resin. These kinds of resins have excellent adhesion strength and stability for high heat and are thus appropriate for conducting the heat generated from the light emitting diode elements 14 mounted on the metal pattern layer 12. The ceramic powder may include at least one of an aluminum oxide ceramic powder, an aluminum nitride ceramic powder, a titanium dioxide ceramic powder, and a silicon dioxide ceramic powder. These ceramic powders have high thermal conductivity and a high electrical insulation level and are thus appropriate for conducting the heat generated from the light emitting diode elements 14 mounted on the metal pattern layer 12. A content of the ceramic powders may be 30 to 80 wt % based on the resin. When the content of the ceramic powders is less than 30 wt % based on the resin, thermal conduction capability of the insulating resin adhesive layer 13 is insufficient, such that a bottleneck phenomenon may occur in conducting the heat from the metal pattern layer 12 to the first fiber fabric layer 11. In addition, when the content of the ceramic powders exceeds 80 wt %, a problem may occur in adhesion strength between the insulating resin adhesive layer 13 and the metal pattern layer 12 or the first fiber fabric layer 11.

The metal pattern layer 12 is a layer on which a thin plate (metal foil) famed of a metal forms a predetermined pattern. Here, the metal foil may be generally famed of copper. The light emitting diode elements 14 are attached onto the metal pattern layer 12. Flip-on-chip light emitting diodes may be used as the light emitting diode elements 14.

The light emitting diode elements 14 irradiate photon therapy light including near infrared light and far infrared light. That is, first sub light emitting diodes 141 and second sub light emitting diodes 142 are alternately installed. Here, the first sub light emitting diodes 141 have a wavelength band of 600 to 680 nm and the second sub light emitting diodes 141 have a wavelength band of 800 to 980 nm to activate the derma layer as well as the epidermis layer, thereby making it possible to allow the nourishing components of the mask pack M to be well permeated into the skin. In addition, the third sub light emitting diode having a wavelength band of 700 to 800 nm may be additionally installed.

Meanwhile, a CNT layer having excellent thermal conductivity may be further added between the first fiber fabric layer 11 and the second fiber fabric layer (which may be referred to herein as the heat dissipation sheet 40). The CNT layer is formed in order to allow the heat generated from the light emitting diode elements 14 to be more rapidly conducted to the second fiber fabric layer. Meanwhile, when the metal pattern layer 12 is formed of copper or aluminum having excellent ductility, entire ductility may be significantly increased, and a heat dissipation effect may be maximized.

The second fiber fabric layer attached to the first fiber fabric layer 11 serves as the heat dissipation sheet 40. A lower portion of the second fiber fabric layer is exposed to the air as it is. The surface exposed as described above may be called a heat dissipation surface.

According to such a configuration, one surfaces of a plurality of woven fibers of the second fiber fabric layer (the heat dissipation sheet 40) are exposed to the air as they are, such that surface areas of portions of the second fiber fabric layer (the heat dissipation sheet 40) in contact with the air are significantly increased.

Therefore, the heat generated by the light emitting diode elements 14 mounted on the metal pattern layer 12 may sequentially pass through the metal pattern layer 12, the insulating resin adhesive layer 13, and the first fiber fabric layer 11, be transferred to the second fiber fabric layer (the heat dissipation sheet 40), and be then effectively dissipated to the air. In such a heat dissipation process, a convection action of the air that the second fiber fabric layer (the heat dissipation sheet 40) is in contact with more effectively enhances the heat dissipation function by a relatively wide surface area of the second fiber fabric layer (the heat dissipation sheet 40).

The second fiber fabric layer (the heat dissipation sheet 40) may be configured to include internal fiber bundles 42 arranged in parallel with each other and external fiber bundles 41 including first external fiber bundles 41-1 surrounding outer surfaces of the internal fiber bundles 42 in a shape of a first sine wave and second external fiber bundles 41-2 surrounding outer surfaces of the internal fiber bundles 42 while intersecting with the first external fiber bundles 41-1 in a shape of a second sine wave having a phase of 180° with respect to the first sine wave.

Here, the internal fiber bundles 42 are configured to have thermal conductivity higher than those of the first and second external fiber bundles 41-1 and 41-2.

The second fiber fabric layer (the heat dissipation sheet 40) may include a heat converging layer and a heat radiating layer when it is divided depending on their functions. The heat converging layer, which is an upper layer of the second fiber fabric layer (the heat dissipation sheet 40), is a portion that directly converges the heat transferred from the first fiber fabric layer 11. To the contrary, the heat radiating layer, which is a portion exposed to the outside, outwardly radiates the heat converged in the heat converging layer.

Here, thermal conductivity of the internal fiber bundles 42 disposed at the center is more excellent than those of the first and second external fiber bundles 41-1 and 41-2. Therefore, the heat in the heat converging layer is more rapidly conducted to the internal fiber bundles 42 having the excellent thermal conductivity, and the heat in the internal fiber bundles 42 is conducted to the first and second external fiber bundles 41-1 and 41-2 having wide surface areas, such that heat dissipation efficiency becomes excellent. In other words, here, the heat converging layer may converge the heat since the heat moves from a wide curved surface toward the center of the curved surface. To the contrary, the heat radiating layer may radiate the heat since it dissipates the heat from the center through the wide curved surface.

The internal fiber bundles are arranged to be extended in a direction perpendicular to paper drawn in the present drawing. The internal fiber bundles may be arranged in parallel with each other so as to form rows.

The first and second external fiber bundles 41-1 and 41-2 surround the external surfaces of the internal fiber bundles 42 to form closed curved lines. In detail, in the present exemplary embodiment, the external fiber bundles 41 form closed curved lines having a substantially oval shape with respect to the internal fiber bundles 42, and surround the outer surfaces of the internal fiber bundles 42. The first external fiber bundles 41-1 and the second external fiber bundles 41-2 are arranged to form sine waves having phases opposite to each other while intersecting with each other. Considering the shapes of the external fiber bundles having the shapes of the sine waves as described above, the first external fiber bundles 41-1 may be called 'first sine wave fiber bundles', and the second external fiber bundles 41-2 may be called 'second sine wave fiber bundles'.

The second fiber fabric layer (the heat dissipation sheet 40) as described above has thermal conductivity higher than that of the first fiber fabric layer 11, and does not have a problem even though it has electrical conductivity. Therefore, metal powders may be included in the second fiber fabric layer (the heat dissipation sheet 40) to further increase the thermal conductivity.

The device for activating a mask pack may be configured using a plastic flexible substrate besides being configured using the fiber substrate as described above.

In another example of a light emitting sheet of the device for activating a mask pack according to an exemplary embodiment of the present invention, the light emitting sheet may be configured to include a flexible substrate, a metal pattern layer, light emitting diode elements, and a metal reinforcing plate. Here, since the metal pattern layer and the light emitting diode elements are the same as those described above, a description therefor will be omitted for simplification.

The flexible substrate is famed of a plastic material, and is formed at a very thin thickness in order to have sufficient ductility depending on a curved surface of a face. To this end, the flexible substrate in the present invention may be formed of a fiberglass reinforcement epoxy laminate (FR4), and may have a thickness of 0.1 mm to 0.5 mm.

The metal reinforcing plate for reinforcing damage to the flexible substrate due to warpage of the flexible substrate may be formed on a lower surface of the flexible substrate.

According to an exemplary embodiment of the present invention having the configuration described above, the device for activating a mask pack capable of improving an effect of the mask pack and improving convenience of the user by reducing a use time of the mask pack may be provided.

In addition, according to an exemplary embodiment of the present invention, both of the derma layer and the epidermis layer are activated, such that the nourishing components of the mask pack may be deeply permeated into the skin.

Further, according to an exemplary embodiment of the present invention, the burn of the wearer due to the heat generated in the LED may be prevented.

In the device for activating a mask pack and the photon therapy mask pack device as described above, the configuration and the method of the exemplary embodiments described above are not restrictively applied. Rather, all or some of the respective exemplary embodiments may be selectively combined with each other so that the exemplary embodiments may be variously modified.

What is claimed is:

1. A device for activating a mask pack, the device comprising:
    a light emitting sheet comprising:

a first fiber fabric layer including a first surface and a second surface and comprising a shape corresponding to a shape of a face of a wearer of the mask pack, the first fiber fabric layer having a property for being closely adhered to the face of the wearer;

a metal pattern layer attached to the first surface of the first fiber fabric layer, the metal pattern layer comprising a metal foil with a predetermined pattern;

a plurality of light emitting diode elements disposed on the metal pattern layer and configured to emit a photon therapy light such that a nourishing component of the mask pack is better permeated into a skin of the face of a wearer; and an insulating resin adhesive layer disposed between the metal pattern layer and the first fiber fabric layer;

an adhesive film layer to be coupled to the mask pack, wherein the adhesive film layer comprises:

a transparent silicon resin, and an embossed surface to increase an adhesion property of the adhesive film layer with the mask pack, wherein the adhesive film layer is configured to cover the light emitting sheet and be disposed on a front surface of the device in direct contact with the mask pack for activating the mask pack, wherein the adhesive film layer covers the metal pattern layer and the plurality of light emitting diode elements, and wherein the adhesive film layer includes a surface configured to generate scattering or refraction of the photon therapy light to improve an effect of the photon therapy light; and a power supplying module supplying power to the plurality of light emitting diode elements in the light emitting sheet.

2. The device for activating the mask pack of claim 1, wherein each of the plurality of light emitting diode elements comprises a flip-on-chip light emitting diode.

3. The device for activating the mask pack of claim 1, wherein the adhesive film layer further comprises a plurality of wrinkle parts configured in a concentric circle shape formed on the surface of the adhesive film layer.

4. The device for activating the mask pack of claim 1, further comprising a second fiber fabric layer attached to the second surface of the first fiber fabric layer.

5. The device for activating the mask pack of claim 4, wherein the first fiber fabric layer has an electrical insulation property, and the second fiber fabric layer has a thermal conductivity more excellent than that of the first fiber fabric layer.

6. The device for activating the mask pack of claim 5, wherein the second fiber fabric layer includes:

a plurality of external fiber bundles formed to be orthogonal to each other; and a plurality of internal fiber bundles formed in a space formed by the plurality of external fiber bundles.

7. The device for activating the mask pack of claim 1, wherein each of the plurality of light emitting diode elements includes:

a first sub light emitting diode having a wavelength band of 600 to 680nm, and a second sub light emitting diode having a wavelength band of 800 to 980nm; and wherein the first sub light emitting diode and the second sub light emitting diode are alternately installed on the metal pattern layer.

8. The device for activating the mask pack of claim 1, further comprising a coupling hole formed on the adhesive film layer in order to securely attach the mask pack to the adhesive film layer.

9. A photon therapy mask pack device comprising:

a mask pack;

a light emitting sheet;

an adhesive film layer covering the light emitting sheet, wherein the mask pack is in direct contact with the adhesive film layer;

and a power supplying module supplying power to the light emitting sheet;

wherein the light emitting sheet comprises:

a first fiber fabric layer having a shape corresponding to a shape of a face of a wearer, the first fiber fabric layer having a property for being closely adhered to the face of the wearer;

a metal pattern layer disposed on a first surface of the first fiber fabric layer, the metal pattern layer comprising a metal foil with a predetermined pattern;

an insulating resin adhesive layer disposed between the first fiber fabric layer and the metal pattern layer for attaching the first fiber fabric layer to the metal pattern layer; and a light emitting diode element attached onto the metal pattern layer and configured to irradiate a photon therapy light such that a nourishing component of the mask pack is better permeated into a skin of the face of the wearer;

wherein the adhesive film layer covers the metal pattern layer and the light emitting diode element and configured to be in direct contact with the mask pack, wherein the power supplying module supplies power to the light emitting diode element to allow the nourishing component of the mask pack to be well permeated into the skin of the wearer, wherein the adhesive film layer comprises a transparent silicone resin, and wherein the adhesive film layer includes a surface configured to generate scattering or refraction of the photon therapy light to improve an effect of the photon therapy light, and the surface of the adhesive film layer for the face of the wearer comprises an embossed surface in order to increase an adhesion property of the adhesive film layer with the mask pack.

10. The device for activating the mask pack of claim 9, wherein the light emitting diode element comprises a flip-on-chip light emitting diode.

11. The photon therapy mask pack device of claim 9, wherein a plurality of wrinkle parts configured in a concentric circle shape are formed on the surface of the adhesive film layer.

12. The photon therapy mask pack device of claim 9, further comprising a second fiber fabric layer attached to the second surface of the first fiber fabric layer.

13. The photon therapy mask pack device of claim 9, wherein the first fiber fabric layer has an electrical insulation property, and a second fiber fabric layer has a thermal conductivity more excellent than that of the first fiber fabric layer.

14. The photon therapy mask pack device of claim 13, wherein the second fiber fabric layer includes:

a plurality of external fiber bundles formed to be orthogonal to each other; and a plurality of internal fiber bundles formed in a space formed by the plurality of external fiber bundles.

15. The photon therapy mask pack device of claim 9, wherein the light emitting diode element includes:
- a first sub light emitting diode having a wavelength band of 600 to 680nm; and
- a second sub light emitting diode having a wavelength band of 800 to 980nm;
- wherein the first sub light emitting diode and the second sub light emitting diode alternately installed on the metal pattern layer.

16. The photon therapy mask pack device of claim 9, further comprising a coupling hole formed on the adhesive film layer in order to securely attach the mask pack to the adhesive film layer.

* * * * *